United States Patent [19]

Nakano et al.

[11] Patent Number: 5,541,288
[45] Date of Patent: Jul. 30, 1996

[54] PEPTIDE HAVING ELASTASE INHIBITORY ACTIVITY AND PRODUCING METHOD THEREOF

[75] Inventors: Shigeru Nakano, Shiga; Toshiyuki Mabuchi, Kusatsu; Miki Tada, Ohtsu; Yasuo Taoda, Shiga; Dan Sugino, Ohtsu; Yoshio Kono, Kyoto; Kaoru Nishimura, Kusatsu; Minoru Okushima, Hirakata, all of Japan

[73] Assignee: Nissin Shokuhin Kabushiki Kaisha, Osaka, Japan

[21] Appl. No.: 325,243

[22] PCT Filed: Feb. 21, 1994

[86] PCT No.: PCT/JP94/00284

§ 371 Date: Dec. 16, 1994

§ 102(e) Date: Dec. 16, 1994

[87] PCT Pub. No.: WO94/19371

PCT Pub. Date: Sep. 1, 1994

[30] Foreign Application Priority Data

Feb. 22, 1993 [JP] Japan .................... 5-031758

[51] Int. Cl.$^6$ .................... A61K 38/00; C07H 21/04; C12P 21/06; C12N 1/20
[52] U.S. Cl. .................... 530/324; 435/69.2; 435/252.3; 435/320.1; 536/23.1
[58] Field of Search ................. 435/69.2, 252.3, 435/320.1; 530/324; 536/23.1

[56] References Cited

U.S. PATENT DOCUMENTS

| | | | |
|---|---|---|---|
| 5,409,895 | 4/1995 | Morishita et al. | 514/12 |
| 5,451,659 | 9/1995 | Morishita et al. | 530/324 |

FOREIGN PATENT DOCUMENTS

0486001A1  5/1992  European Pat. Off. ........ C12N 15/15

OTHER PUBLICATIONS

Morii et al. (1985) Biol. Chem. Hoppe–Seyler 366: 19–21.
Barrett, Alan J., "The Possible Role of Neutrophil Proteinases in Damage to Articular Cartilage", *Agents and Actions*, 8:11–18 (1978).
Carp et al., "Potentail Mediator of Inflammation: Phagocyte–Derived Oxidants Suppress the Elastase–Inhibitory Capacity of Alpha$_1$–Proteinase Inhibitor in Vitro", *J. Clin. Invest.*, 66:987–995 (1980).

Carrell et al., "Structure and Variation of Human $\alpha_1$–Antitrypsin", *Nature*, 298:329–334 (1982).
Ford et al., "Current Status of Alpha–1–Antitrypsin Replacement Therapy: Recommendations For the Management of Patients With Severe Hereditary Deficiency", *Can. Med. Assoc. J.*, 146:841–844 (1992).
Janoff et al., "Possible Mechanisms of Emphysema in Smokers", *Am. Rev. Respir. Dis.*, 116:65–72 (1977).
Janoff, Aaron Ph.D., "Elastase In Tissue Injury", *Ann. Rev. Med.*, 36:207–216 (1985).
Laemmli, U. K., "Cleavage of Structural Proteins During the Assembly of the Head of Bacteriophage T4", *Nature*, 227:680–685 (1970).
Ohnishi et al., "Protective Effects of Urinary Trypsin Inhibitor in Experimental Shock", *Jpn. J. Pharmacol.*, 39:137–144 (1985).
Ohnishi et al., "Pharmacological activities of a trypsin inhibitor, urinastatin", *Oyo Yakuri*, 31(3):663–675 (1986).
Sanger et al., "DNA Sequencing With Chain–Terminating Inhibitors", *Proc. Natl. Acad. Sci.* (USA), 74:5463–5467 (1977).
Wachter et al., "Kunitz–Type Proteinase Inhibitors Derived by Limited Proteolysis of the Inter–$\alpha$–Trypsin Inhibitor, IV$^t$ $_{1-3}$]: The Amino Acid Sequence of the Human Urinary Trypsin Inhibitor Isolated by Affinity Chromatography", *Hoppe–Seyler's Z. Physiol. Che,. Bd,.* 362:1351–1355 (1981).
*Area of Chemical Therapy*, 5:1455–1459 (1989).
*Bulletin of Pharmacological Society of Japan*, 99:93–107 (1992).
*Megabolism*, 29/1:41–49 (1992).
*Genetic–Engineering Handbook*:19–26, Yodo–sha eds., (1991).

*Primary Examiner*—Robert A. Wax
*Assistant Examiner*—Lisa J. Hobbs
*Attorney, Agent, or Firm*—Marshall, O'Toole, Gerstein, Murray & Borun

[57] ABSTRACT

The present invention relates to a novel peptide having a pharmacologically useful activity and a producing method thereof. The peptide is prepared by altering a part of amino acids which constitute a peptide having a normal protease inhibitory activity.

26 Claims, 2 Drawing Sheets

PEPTIDE HAVING ELASTASE INHIBITORY ACTIVITY AND PRODUCING METHOD THEREOF

FIELD OF THE INVENTION

The present invention relates to a novel peptide having a pharmacologically useful activity and a producing method thereof. The peptide is prepared by altering a part of amino acids which constitute a peptide having a normal protease inhibitory activity.

BACKGROUND OF THE INVENTION

Elastase, which is one of the proteolytic enzymes, has been said to play an important role in metabolism of living tissue. In particular, elastase, which is secreted from neutrophils which are one type of lymphocyte, is involved in infectious disease and inflammation of tissue, and may act in protection against infection and regeneration of damaged tissue. A protein having elastase inhibitory activity is also produced in the living body, and it acts to prevent excessive degradation of the living tissue by neutralizing the excess elastase activity [Ann. Rev. Med., 36:207–216, (1985)].

As stated above, the balance between the activity of elastase and that of elastase inhibitory protein is strictly regulated and maintained in the living body. When this balance is disturbed various diseases can result. For example, when elastase activity is enhanced, diseases such as pulmonary emphysema, idiopathic pulmonary fibroma, and adult respiratory distress syndrome (ARDS) are caused in the lung [Metabolism, 29:41–49, (1992)], and an increase of neutrophil elastase activity in the joints is thought to be involved in generation of diseases such as rheumatoid arthritis and deformative arthritis [Agents Actions, 8:11–18 (1978); Bulletin of Pharmacological Society of Japan, 99:93–107 (1992)]. Further, elastase is thought to be involved in generation of acute and chronic inflammatory diseases [Ann. Rev. Med., 36:207–216 (1985)].

α 1-anti-trypsin (hereinafter referred to as "α 1-AT") has been well known as one of the elastase inhibitory proteins which modulate the activity of elastase in the living body. α 1-AT exists in blood in a large amount and plays a role in inhibiting and neutralizing elastase activity [Nature, 298:329–334 (1982)]. However, since α 1-AT is very susceptible to oxidization, when air containing high levels of peroxide owing to smoking and air pollution is inhaled continuously, α 1-AT is oxidized by the inhaled peroxide in the lung, and the elastase inhibitory activity thereof may be lost [Am. Rev. Respir. Dis., 116:65–72 (1977)].

Further, α 1-AT is oxidized by oxygen released from leukocytes which migrate to the portion in the lung inflamed by the inhalation of the polluted air containing inflammable materials, and it loses elastase inhibitory activity [J. Clin. Invest., 66:987–995 (1980)]. Such inactivation of α 1-AT leads to a condition of an excess elastase activity in the limited portion in the lung, then the alveolus tissue is degraded by the excess elastase, and results in lung diseases such as pulmonary emphysema [Area of Chemical Therapy, 5:1455–1459 (1989)]. When bacteria infect the lung, and inflammation is therefore caused at the limited portion in the lung, α 1-AT is also inactivated and the lung tissue may be destroyed because leukocytes such as neutrophil migrate to the inflammatory site by the infection and they secrete a large amount of active oxygen and elastase [Metabolism, 29:41–49 (1992)].

In order to prevent and treat the diseases involving an elastase aforementioned, it has been said that administration of an elastase inhibitory substance such as α 1-AT into blood or tissue changed pathologically may be effective [Can. Med. Assoc. J., 146:841–844 (1992)]. However, it is necessary to use the α 1-AT derived from human to avoid an antigen-antibody reaction as a side-effect. Therefore obtaining enough α 1-AT for prevention and treatment has been difficult.

In addition, since pathogenic virus derived from human may remain in the purified α 1-AT products, when an elastase inhibitory substance such as α 1-AT is extracted and purified from human blood, this is a factor that has presented difficulties in using α 1-AT derived from human for prevention and treatment of diseases induced by elastase.

Further, although a spray-inhalation method by nebulizer is used commonly for administrating the drugs against lung diseases, since α 1-AT is very susceptible to oxidization as stated above, elastase inhibitory activity is inactivated by oxidation with the spray and, if administration is performed by another route, is also inactivated with active oxygen generated from various cells in the living body.

Furthermore, application of chemically synthesized low molecular weight elastase inhibitors to the above-referenced diseases has also been studied. However, since substances to be administrated in these methods are foreign substances to the living body, when these are administrated into the living body, undesirable side-effects, such as toxicity, may result. Then, these chemically synthesized low molecular weight elastase inhibitors may also inhibit an activity of the other proteolytic enzymes having important physiological activities, and this lack of specificity restricts the usage of these chemically synthesized low molecular weight elastase inhibitors as drugs of choice against the diseases induced by elastase.

Though elastase inhibitor is thought to be quite useful for preventing and curing the diseases induced by elastase, such as pulmonary emphysema, there are various problems discussed above for the pharmaceutical application of inhibitors derived from human such as α 1-AT and chemically synthesized low molecular weight elastase inhibitors, and clinical application thereof as a medicine has therefore yet to be accomplished.

SUMMARY OF THE INVENTION

The present invention was established in view of the problems in the art aforementioned and the purposes thereof are to provide a novel peptide which is quite useful pharmacologically as a drug for the prevention and the treatment of diseases caused by elastase. The peptides have strong inhibitory activity against the human neutrophil elastase and anti-oxidation, and less ability to raise an antigen-antibody reaction. The peptides were prepared by altering a part of amino acid sequence of the C-terminal domain (hereinafter referred to as "HI-8") in human-urinary-trypsin-inhibitor (Ulinastatin, hereinafter referred to as "UTI") which is distributed in the market as a medicine and has confirmed desirable effects in the human. The invention provides a producing method thereof through genetic engineering techniques using recombinant microorganisms.

More specifically, the present invention relates to novel peptides, genes encoding said peptides, a recombinant microorganisms containing said genes, and a producing method of said novel peptides using said recombinant microorganisms, wherein said peptides has a pharmacologically useful elastase inhibitory activity obtained by altering, with a genetic or a proteinic engineering technique, a part of amino acid sequences within approximately 7.3 kDa fragment [*Hoppe-Seyler's Z. Physiol. Chem. Bd.*, 362:1351–1355 (1981)] of the C-terminal domain of human-urinary-trypsin inhibitor prepared by limited degradation of UTI in the presence of excess proteolytic activity in vivo or trypsin in vitro and having a trypsin inhibitory activity.

UTI is a trypsin inhibitor contained in human urine and is a protein which has been applied as a purified product from human urine in the treatment of acute circulatory defects as well as pancreatitis. Its desirable effect upon intravenous administration has also been confirmed [*Digest. Dis. Sci.*:26–32 (1984; *Jpn. J. Pharmacol.*, 39:137–144 (1985)]. The approximately 7.3 kDa domain of C-terminal portion of UTI having trypsin inhibitory activity is contained in the human urine together with UTI, and is thought to be produced through limited hydrolosis by a trypsin-like enzyme in the living body.

The present inventors focused on HI-8 which is thought to be very safe for the human and tried to reduce trypsin inhibitory activity in comparison with that of normal HI-8, and to generate independent novel strong elastase inhibitory activity by altering a part of amino acid sequence which is adjacent to a core portion relating to the activity. First of all, the three dimensional structure of a protein complex of HI-8 and human neutrophil elastase was deduced with a computer program for deducing three-dimensional structure of proteins. The site of specific binding to human neutrophil elastase and the kinds of amino acids, which are non-sensitive to the oxidation were identified. Amino acids were chosen for alteration based on study of the binding site therebetween in spatial axis.

Furthermore, in order to use recombinant genetic techniques suitable for large scale production, simple purification, and avoiding incorporation viruses derived from humans, *Escherichia coli* was used as a recombinant host for DNA encoding the amino acid sequence of HI-8 and an appropriate secretion signal peptide. The DNA was chemically synthesized with codon usage suited thereto, and said DNA was cloned into an appropriate expression vector. Then, site-directed mutagenesis was performed on the plasmid containing this synthesized DNA to introduce sequences encoding the amino acids determined from said computer analysis. Peptides encoded by mutated DNA so obtained were expressed by the recombinant host bacteria, evaluated for inhibitory activities compared to the human neutrophil elastase, and novel peptides having strong elastase inhibitory activity were selected.

As a result, the Ki value against the human neutrophil elastase which is about $6.9 \times 10^{-7}$M for non-altered HI-8 was reduced to about $6 \times 10^{-10}$M by altering the 3rd, 11th, 15th, 18th, and 46th amino acid residues from N-terminal of a peptide to the amino acids respectively shown in the Example.

In the other words, the present inventors have discovered that strong elastase inhibitory activity could be obtained by intentionally altering a part of the amino acid sequence of HI-8. The amino acid sequence, which has been elucidated in the present invention, of altered HI-8 having elastase inhibitory activity is set out in SEQ ID NO: 1.

As is shown in the following Examples concerning inhibitory effects of the altered peptides on human neutrophil elastase, preferably the 15th amino acid in the sequence of SEQ ID NO: 1 is a hydrophobic amino acid residue, such as isoleucine, leucine, valine. The strongest inhibition against human neutrophil elastase was obtained by the most preferred altered peptide, wherein the 11 th amino acid was changed to glutamic acid, and the 46th amino acid was changed to glutamine.

Although this altered peptide of HI-8 comprises an amino acid sequence having the sixty-six amino acids set out in SEQ ID NO: 1, an inhibitory activity against the human neutrophil elastase will be obtained, even if a part of amino acid sequence in N-terminal side or C-terminal side is deleted. In other words, the present invention encompasses, as a matter of course, a core structure of altered HI-8 which inhibits the human neutrophil elastase.

Further, purposes of the present invention will be achieved by substituting, with a corresponding portion in another serine protease inhibitor, amino acid sequences which lie adjacent to an active site of altered HI-8, for example, a substituted peptide containing at least the four amino acids N-terminal and C-terminal to the 15th amino acid in the peptide of the present invention.

Altered HI-8 peptides of the present invention may be produced by chemically synthesizing DNA which encodes the sequences thereof, inserting the DNA downstream of an appropriate promoter, introducing the DNA into a preferable host such as *Escherichia coli*, *Bacillus subtilis*, or an animal cell, and culturing the transformants.

Alternatively, DNA which codes a target altered peptide can be obtained by isolating DNA for UTI from an appropriate human cDNA library, and introducing the required alteration(s) into this DNA by site-directed mutagenesis.

Secretion of the altered peptide of the present invention into the culturing liquid of the recombinant host is useful for effectively purifying the altered peptide. An appropriate signal sequence for the secretion is inserted upstream of the DNA encoding the altered peptide. For example, secretion of the peptide into the culturing liquid is possible if a host is animal cell, in addition thereto, secretion of the peptide into the culturing liquid or periplasmic space is also possible when a host is *Escherichia coli*.

Producing the altered peptide of the present invention as a stable fusion protein with a host protein by connecting it to the other appropriate protein is also useful. Expressed fused proteins can be isolated and purified through a technique using a character such as antigenicity of the connected protein, or the target altered peptide can be isolated and purified by site-specifically cleaving the fusion protein so obtained with enzyme which is appropriate for proteolysis or chemically cleaving technique which is specific to the sequence of the connected peptide.

Further, the altered peptide of the present invention can be produced, by adding SD sequence as well as an appropriate promoter such as lac, trc, or tac upstream of DNA sequences which encodes the altered peptides, adding an appropriate termination signal downstream thereof, and introducing the sequences into host microorganism in a plasmid appropriate to the host, and culturing the obtained transformants. When the targeted peptide is expressed in bacterial cells an ATG codon, the initiation signal for translation, is added to 5' end of the gene. When the altered peptide is secreted to the culturing liquid or periplasm of the host cell, DNA which codes signal peptide is adjoined to the upstream of the gene. By altering the amino acid sequence of this connected portion by site-directed mutagenesis, digestion of the signal peptide to give a desired N-terminal sequence of the altered peptide may also be possible. Then, by an addition of inducer to the medium to enhance the function of the promoter and increase the amount per unit time of expression, the altered peptide in a form of inclusion body can be produced in cytoplasm in the absence of signal peptide or in periplasm in the presence of the signal peptide.

When the altered peptide of the present invention is produced using a microorganism host, an expression product wherein the preferable S—S bond between the cysteine residues is not formed and the three-dimensional structure of the peptide which is not the same as the native type, may be produced. Expression in inclusion bodies affords partial purification, however, obtaining an active altered peptide is difficult in view of lack of formation of the S—S bond. In these cases, by purifying the peptide under the reducing conditions to reduce inappropriate S—S bonds with an appropriate reducing agent, and by applying a re-oxidizing method to the peptide according to the characteristic of it, the activity can be recovered.

The altered peptide according to the present invention is easily separated and purified from the reaction solution, bacterial cells, or culturing liquid with a combination of conventional separation and purification techniques. These techniques to be employed comprise a method of using solubility of the product such as salting-out or solvent-precipitation; a method of utilizing a difference on molecular weight such as dialysis, ultrafiltration, gel-filtration or SDS-polyacrylamide gel electrophoresis; a method of utilizing an electric affinity such as ion-exchange chromatography; a method of utilizing a difference in hydrophobicity such as reverse phase chromatography; or a method of utilizing a difference in isoelectric point such as isoelectrofocusing.

EXAMPLE 1

Construction of A Gene Encoding C-terminal Peptide (HI-8) of UTI

Figure 2:
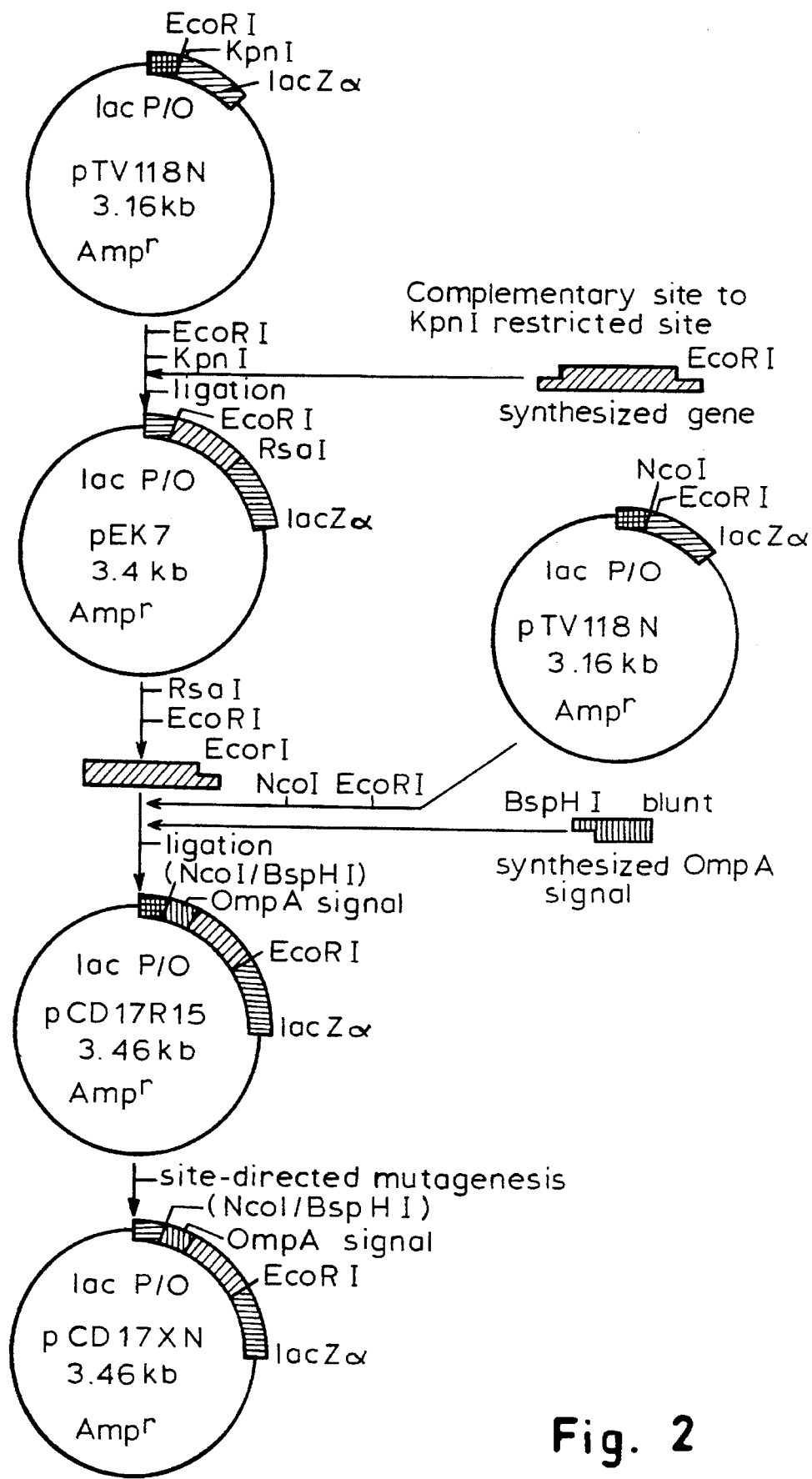
FIG. 2 illustrates a process for constructing the expression plasmid of the present invention.

Firstly, the construction of the gene coding for a peptide corresponding to the C-terminal side of UTI, as a starting gene for preparing mutants, is explained with reference to FIG. 2.

Based on the amino acid sequence of UTI disclosed in the thesis of *Hoppe-Seyler's Z. Physiol. Chem.*, 362:1351–1355 (1981), a gene having a structure set out in SEQ ID NO: 2 which codes C-terminal side region ($Thr^{78}$-$Leu^{143}$) containing trypsin inhibitory active site of UTI was designed by selecting codons which are used frequently in *Escherichia coli*, successively arranging one of the termination signal codons for translation, TGA, at 3' end of the structural gene, adding a Trp terminator downstream thereof, and providing restriction-enzyme-recognition-sites (KpnI digestable site at 5' end, EcoRI digestable site at 3' end) at both ends for the construction of said starting gene. Then, this gene was divided according to the ten sections shown in FIG. 1 and ten oligonucleotides each encoding one section were chemically synthesized, each having one of the base sequences set out in SEQ ID NOs: 3 through 12 [corresponding to the sequences (1) through (10) in FIG. 1]. These oligonucleotides were synthesized by using phosphoamidite with an automatic DNA synthesizer (Model 381A, Applied Biosystems). Purification of the synthesized oligonucleotides was performed according to a manual for purification of the manufacturer Applied Biosystems. That is to say, protective groups of the bases were released by heating concentrated ammonia solution containing synthesized oligonucleotides at 55° C. for a whole day and night, and prepurification was performed with OPC cartridges (Applied Biosystems). Further, if necessary, the 5' end of the synthesized oligonucleotide was phosphorylated through a reaction at 37° C. for one hour in a solution of 1 mM $MgCl_2$, 0.5 mM dithiothreitol, 1 mM ATP and 50 mM Tris-HCl (pH 7.6) containing 16 units of polynucleotidekinase (Toyobo).

Then, the oligonucleotides were applied to polyacrylamide gel electrophoresis (gel phase 20% ) containing 7M urea, the gel was stained with ethidium bromide, and bands corresponding to targeted oligonucleotide appearing on a long wave length (365 nm) ultra violet generator were excised. 1 ml of the solution for the extraction of DNA [20 mM Tris-HCl (pH 8.0), 1.5 mM EDTA] was added to these samples, the samples were shaken overnight at 37° C. and the solution containing the synthesized oligonucleotides was obtained through a purification by applying the supernatant after centrifugation to a desalting-column.

Figure 1:
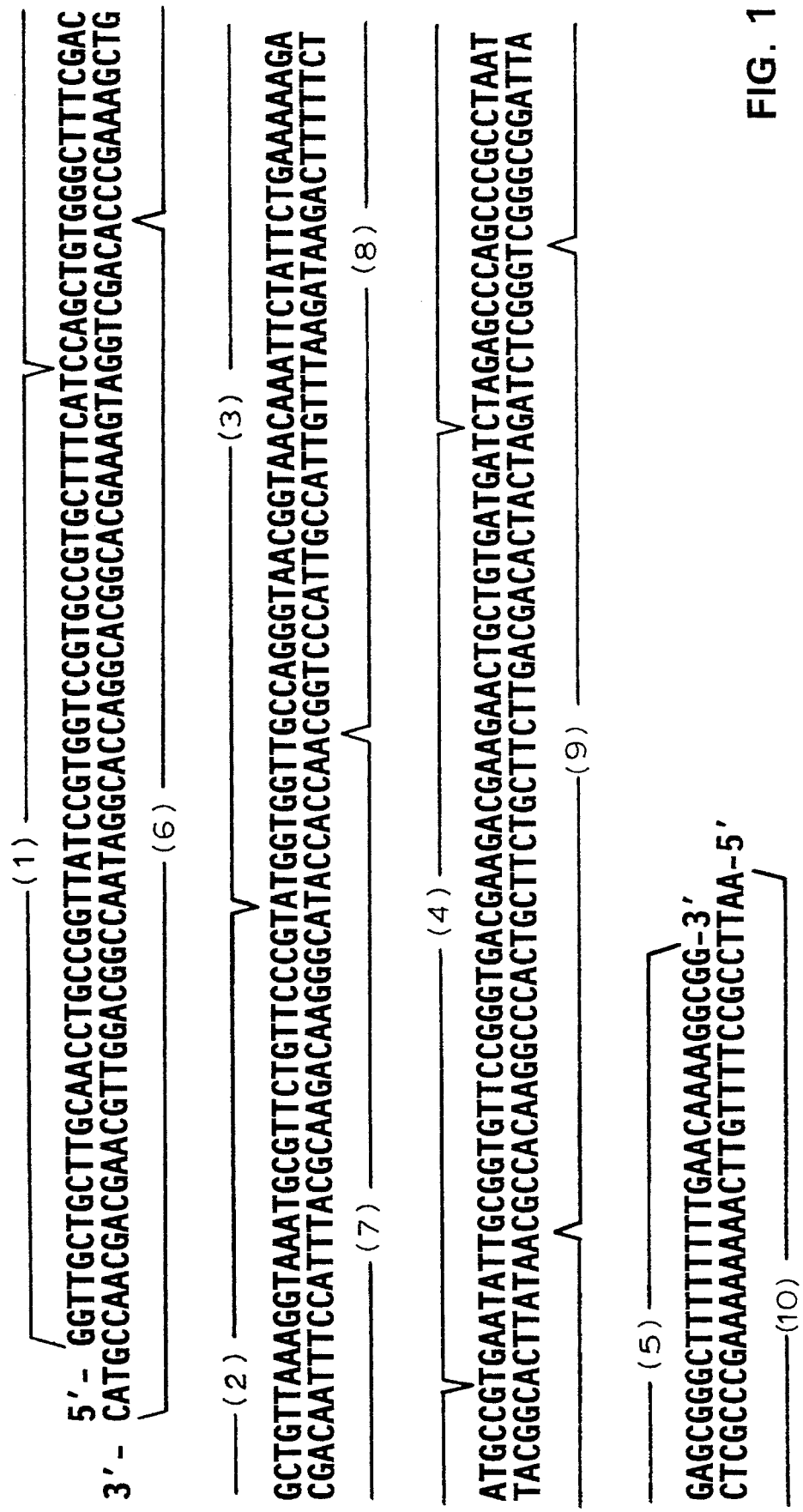
FIG. 1 comprises the ten oligonucleotides forming the gene having the structure set out in SEQ ID NO: 2.

Each pair of complementary strands shown in FIG. 1, for example, base sequences (1) and (6), were mixed in 50 mM Tris-HCl (pH 7.6), 10 mM $MgCl_2$ in molar equivalents, incubated at 90° C. for 5 minutes, and annealed by gradually cooling to room temperature. Annealed synthesized DNA fragments were isolated by poly-acrylamide gel electrophoresis (gel phase 10%) not containing urea, and purified by similar methods referred to previously in purification of synthesized oligonucleotides.

Plasmid pTV118N (Takara-Shuzo) was digested with the restriction enzymes EcoRI and KpnI, the linearized fragment was separated on agarose gel electrophoresis, and the target DNA band was excised from the gel. Samples prepared by freezing the gel block at −80° C. for one hour and rapidly heated up at 370° C. were filtrated using a centrifugation filter (Milipore) of 0.1 μm pore size.

Filtrated samples were extracted with phenol reagent, then precipitated with ethanol, and the linearized plasmid was purified and collected. Collected plasmids and five pairs of the synthesized DNA fragments [i.e., pairs of base sequences (1) and (6), (2) and (7), (3) and (8), (4) and (9), (5) and (10), respectively shown in FIG. 1] were mixed in a solution containing 50 mM Tris-HCl (pH 7.6), 10 mM $MgCl_2$, 10 mM dithiothreitol, 1 mM ATP, and reacted overnight at 4° C. for ligation with 10 units of T4 DNA ligase (Takara-Shuzo).

10 μl of reacted solution was added to 100 μl of *Escherichia coli* (JM109) competent cell suspension (Takara-Shuzo), and transformation was performed according to the manual of the manufacturer Takara-Shuzo. Some of the transformants grown in selective medium (LB-agar plate) containing ampicillin were cultured, and plasmid DNA incorporated thereinto was extracted according to the method using alkali [Yodo-sha, *Genetic-Engineering Handbook*:19–26 (1991)]. Confirmation as to whether or not the target gene and a plasmid containing it were appropriately constructed was performed by deducing a pattern of agarose gel electrophoresis on sample digested with several restriction enzymes, then directly confirming the construction by DNA sequencing by the method using dideoxy nucleotides [*Proc. Nat. Acad. Sci.* USA, 74:5463–5467 (1977)]. The plasmid constructed and selected in the experiment above was named pEK7.

Double strand DNA fragments which were annealed to the synthesized single strand DNA set out in SEQ ID NOs: 13 and 14 were constructed according to the method aforementioned. The fragments encoded the amino acid sequence of the signal peptide of *Escherichia coli* outer membrane protein A (OmpA) and had a BspHI cohesive end at the 5' end of coding strand and a blunt end at 3' end thereof.

This double strand DNA fragment and the 0.25 kb DNA fragment containing synthesized gene produced by digesting said plasmid pEK7 with restriction enzymes RsaI and EcoRI were ligated to between the sites of restriction enzymes NcoI and EcoRI in pTV118N according to the foregoing method.

The resulting plasmid was used to transform *Escherichia coli* (JM109) according to the foregoing method, then, some of colonies grown on LB-agar plate containing ampicillin were cultured and plasmid DNA incorporated thereinto were extracted.

By analysis of the restriction digest pattern on agarose gel electrophoresis and by DNA sequencing by the method using dideoxy nucleotides, the plasmid was confirmed to have the desirable structure (HI-8) and named pCD 17R 15.

EXAMPLE 2

Preparation of Anti-Sera Against Partial Synthesized Peptide ($Ser^{124}$-$Glu^{141}$) of UTI For detection and identification of the expressed peptide, anti-sera against a partial peptide ($Ser^{124}$-$Glu^{141}$ of UTI) of the expressed peptide was prepared.

Firstly, based on the primary structure of UTI, a region which was on the C-terminal side beyond $Thr^{78}$ and had high hydrophilic residues, specifically the region of $Ser^{124}$-$Glu^{141}$ containing amino acid sequence of eighteen residues set out in SEQ ID NO: 15, was selected. Synthesis of the peptide having this amino acid sequence was performed by a solid phase synthesizing method using an automatic peptide synthesizer (Model1431A; Applied Biosystems). Synthesized peptide was separated from the support according to the manual of the manufacturer Applied Biosystems, and purification of the separated synthesized peptide was performed by reverse phase liquid chromatography.

To conjugate the synthesized peptide to ovalbumin, 10 mg of purified synthesized peptide and 3 mg of ovalbumin (Sigma, Type III) were dissolved in 1 ml of distilled water and 30 mg of 1-ethyl-3-(3-dimethylaminopropyl)-carbodiimide hydrochloride (Nakaraitesk) was added and reacted overnight at room temperature under shading.

After dialysing with distilled water, an emulsion prepared by adding equivalent amount of Freund Complete Adjuvant (Difco) to a solution of this synthesized peptide-ovalbumin conjugated product and the emulsion was used for a first immunization (1 ml). Another emulsion prepared by adding Freund Incomplete Adjuvant (Difco) was used for second and successive immunization (0.5 ml). These emulsions were administrated hypodermically once a week to a Japanese white rabbit (11 week old female) and blood was collected when the titer of the specific antibody was raised. Collected blood was left for one hour at room temperature, then overnight at 4° C., and corpuscle mass was removed by centrifugation, and the supernatant thereof was used as anti-sera in successive experiments. This anti-sera reacted little or not at all with protein originating from *Escherichia coli* and had strong reactivity with said synthesized peptide and HI-8.

EXAMPLE 3

Expression Of Recombinant HI-8

*Escherichia coli* (JM109) having the plasmid pCD17R15 (Example 1) was inoculated into 20 ml of TB medium [1.2% Bactotryptone (Difco), 2.4% yeast extract (Difco), 2.31 g/l $KH_2PO_4$, 12.54 g/l $K_2HPO_4$, 0.4% glycerol, (pH 7.0)] containing 100 μg/ml ampicillin, and precultured overnight at 37° C. To become $OD_{600nm}$ to 0.1, an appropriate amount of this preculture was added to 400 ml of TB medium for next culture, and aerobically cultured at 37° C. When $OD_{600nm}$ of this culture became 0.5, isopropylthiogalactoside (IPTG: Nakaraitesk) was added to the medium to be 100 μM of final concentration, and the culture was grown to the late logarithmic growth phase. After culturing, bacterial cells were harvested by centrifugation, and washed with buffer containing 50 mM Tris-HCl (pH 8.0), 1 mM EDTA, 50 mM NaCl.

Washed cells were resuspended in said buffer, the volume of which was 1/20 of the original culturing liquid, and the bacterial cells were lysed on ice by sonication. The suspension of bacterial debris was centrifuged, and recombinant HI-8 was obtained as a precipitate. Then, this precipitate was dissolved into solution of 20 mM Tris-HCl (pH 8.5) containing 8M urea to form a crude recombinant HI-8 solution.

The presence of target recombination HI-8 in this solution was confirmed by Western blot technique using the anti-sera described in Example 2. More specifically, the crude solution was subjected to SDS-polyacrylamide gel electrophoresis (gel phase 20%) [*Nature*, 227:680 (1970)]. After the electrophoresis, separated protein bands appearing in the gel were transferred to the polyvinylidendifluoride membrane (Milipore: hereinafter referred to as "PVDF membrane") with electro blotting device (Tefco) for protein. The PVDF membrane was washed with water and incubated it for one hour in solution prepared by adding skim milk (Difco) to become 1% into 50 mM Tris-HCl (pH 7.6) buffer containing 150 mM NaCl (hereinafter referred to as "TBS buffer"). Then, the membrane was treated in TBS buffer containing 1% skim milk with said anti-sera, incubated for two hours at 4° C. and the PVDF membrane was thoroughly washed with TBS buffer containing 0.05% Tween 20. Further, it was incubated for two hours at 4° C. in TBS buffer containing alkaline-phosphatase-labelled-goat-anti-rabbit IgG solution (Bio-Rad) and 1% skim milk. After thoroughly washing the PVDF membrane again with TBS buffer containing 0.05% Tween 20, the membrane was immersed into reaction solution of alkaline phosphatase [Tris-HCl (pH 9.5) solution containing 5 ml of 10 mM NaCl, 0.5 mM $MgCl_2$ wherein 20 μl of nitrotetrazolium blue solution (prepared by dissolving nitrotetrazolium blue (Dojin) to 50 mg/ml in 70% dimethylformamide solution) and 20 μl of 5-bromo-4-chloro-3-indolylphosphate solution (prepared by dissolving 5-bromo-4-chloro-3-indolylphosphate (Sigma) to 50 mg/ml in dimethylformamide) were added] to initiate a colorimetric reaction. As a result thereof, the band which reacted with said anti-sera appeared at a position of approximately 8 kDa. This molecular weight was substantially identical to the molecular weight calculated from the amino acid sequence of recombinant HI-8.

Recombinant HI-8 peptide expressed by using the plasmid CD17R15 was named R15.

EXAMPLE 4

Uniformalization of N-Terminal Amino Acid in Expressed Peptide

The crude solution of recombinant HI-8 referred to in Example 3 was subjected as a sample to SDS-polyacrylamidegel electrophoresis substantially according to the method of Example 3, and expressed peptide was transferred to PVDF membrane with an electroblotting. Excised PVDF membrane containing this expressed peptide was applied to protein sequencer (Model 471A: Applied Biosystems) and its N-terminal amino acid sequence was analyzed. As a result thereof, in light of proportion on the primary yield, approximately 80% of this sample had the N-terminal amino acid sequence of the sequence set out in SEQ ID NO: 1 indicating that the cleavage of the signal peptide occurred as designed, however, the remaining approximately 20% of the sample started at the fourth amino acid from N-terminus of the originally designed peptide. This seems to have happened because an additional amino acid sequence, which is similar to the digestion-recognition-site of signal peptidase derived from the host, exists around the N-terminus of the target peptide.

Accordingly, in order to make the digestion site of the signal peptide uniform, the alanine residue which is third residue from N-terminus of the peptide which was thought to lead the misrecognition as a signal peptide, was altered to a glycine residue by site-directed mutagenesis using synthesized oligonucleotides.

A kit of Mutan K™ (Takara-Shuzo) was employed for this alteration.

More specifically, firstly, according to a manual of the manufacturer Takara-Shuzo. *Escherichia coli* (CJ236) having pCD 17R15 was infected with helper phage M13K07 to obtain single stranded pCD17R15. Then, an oligonucleotide (wherein 5' end of synthesized oligonucleotide having the sequence of SEQ ID NO: 16) was phosphorylated, annealed to said single strand pCD17R15, and complementary strands were synthesized with DNA polymerase and DNA ligase of the kit. This synthesized DNA was introduced into *Escherichia coli* (BMH71-18 mutS), cultured at 37° C. for one hour, infected with M13K07, and further cultured at the same temperature for 16 to 20 hours. Supernatant from the culture was appropriately diluted, then added to the culturing liquid of *Escherichia coli* (MV1184), and 10 minutes later, an appropriate amount thereof was plated, and formed colonies at 37° C. Some colonies were selected from the grown colonies, and nucleotide sequences with the mutated site on the plasmid incorporated into the selected bacteria were confirmed by dideoxy nucleotide sequencing. A plasmid wherein the desirable mutation was introduced therein was named pCD 17R15G3. The N-terminal amino acid sequence of the peptide which was expressed by *Escherichia coli* (JM109) having pCD17R15G3 was analyzed by the method referred previously, and it was demonstrated that third amino acid residue had been altered to glycine from alanine and that intended signal digestion had been completed because N-terminal amino acid sequence did not indicate any sequence except for the sequence set out in SEQ ID NO: 1.

Altered R15 peptide expressed using this plasmid was named R15G3.

EXAMPLE 5

Preparation of Peptide Having Altered Amino Acid Residues

Site directed mutagenesis was performed by using synthesized oligonucleotides to modify single stranded pCD17R15G3 to produce genes for peptides having altered amino acid residues. Synthesized oligonucleotides including the mutations had the sequences set out in SEQ ID NOs: 17 through 22. The names and sequences of the primers (synthesized oligonucleotides) corresponding to the mutated amino acid residues introduced were listed in the following Table 1.

TABLE 1

| Primer | Sequence |
| --- | --- |
| I15 primer | (15)<br>5'-GGTCCGTGC ATT GCTTTCATC-3' |
| L15 primer | (15)<br>5'-GGTCCGTGC CTG GCTTTCATC-3' |
| V15 primer | (15)<br>5'-GGTCCGTGC GTT GCTTTCATC-3' |
| E11 primer | (11)<br>5'-CCGGTTATC GAA GGTCCGTGC-3' |
| Q46 primer | (46)<br>5'-TAACGGTAACAAATTC CAG TCTGAAAAAGAATGCCG-3' |
| F18I15 primer | (15)    (18)<br>5'-TGC ATT GCTTC TTC CAGCTGTGG-3' |

The altered peptides are named herein by a one letter symbol of the altered amino acid residue (X) followed by the residue numbers of altered residue sites from the N-terminus. In the case of a peptides altered at several residues, indication of 15th altered amino acid residue is noted first. For example, a peptide wherein third and fifteenth amino acids from N-terminus were altered to glycine and isoleucine respectively is indicated as I15G3, and a peptide wherein eleventh amino acid is further altered with glutamic acid is indicated as I15G3E11.

Alteration was performed using a Mutan K kit substantially according to the method referred in Example 4. Alteration of two or more amino acid residues was accomplished by sequentially altering the non-altered residues on the mutated plasmid wherein one of the residues had previously been altered. Nucleotide sequence of each altered site in the mutated plasmid so obtained was confirmed by the sequencing method using dideoxy nucleotides. Mutated plasmids so obtained were indicated, by the kind of introduced amino acid residue (X) and altered position (N=number of residues from N-terminal), as pCD17XN.

The present inventors have been developed ten novel plasmids according to the alteration technique aforementioned and named them pCD17I15G3, pCD17L15G3, pCD17V15G3, pCD17V15G3E11, pCD17V15G3Q46, pCD17V15G3E11Q46, pCD17I15G3E11, pCD 17I15G3Q46, pCD 17I15G3E 11 Q46, and pCD 17I15G3F 18 respectively.

Further, *Escherichia coli* tranformed with pCD17I15G3, pCD17V15G3Q46, pCD17V15G3E11Q46, pCD17I15G3Q46, or pCD17I15G3E11Q46 were prepared, and these *Escherichia coli* were deposited on Feb. 17, 1993, under the conditions of the Budapest Treaty, in the National Institute of Bioscience and Human-Technology Agency of Industrial Science and Technology, at 1–3, Higashi 1 chome, Tsukuba-shi, Ibaraki-ken, JAPAN, particulars of which are as follows:

*Escherichia coli* JM109-pCD17I15G3 containing plasmid pCD 17I15G3 (FERM BP-4556);

*Escherichia coli* JM109-pCD 17V15G3Q46 containing plasmid pCD 17V15G3Q46 (FERM BP-4557)

*Escherichia coli* JM109-pCD17V15G3E11Q46 containing plasmid pCD17V15G3 E11Q46 (FERM BP-4560);

*Escherichia coli* JM109-pCD 17I15G3Q46 containing plasmid pCD17I15G3Q46 (FERM BP-4558); and

*Escherichia coli* JM109-pCD17I15G3E11Q46 containing plasmid pCD17I15G3 E11Q46 (FERM BP-4559). Subject to 37 CFR 1.808(b), all restrictions imposed by the depositor on the availability to the public of the deposited material will be irrevocably removed upon granting of the patent.

EXAMPLE 6

Purification of Recombinant Altered HI-8 from Crude Solution

Crude solutions of recombinant altered HI-8 peptides were prepared from *Escherichia coli* JM109 transformed with a recombinant plasmid of Example 5 according to a method substantially identical to the method referred in Example 3.

More specifically, the crude solutions were dialyzed with 20 mM ammonium acetate (pH 5.5), centrifuged, and the supernatant thereof was applied to ion-exchange chromatography [elution with linear concentration gradient for 10 minutes from 20 mM ammonium acetate (pH 5.5) to ammonium acetate (pH 5.5) containing 0.5M NaCl] using Mono-Q column (Pharmacia). Further, gel-filtration using Superose 12 (Pharmacia) equilibrated with 20 mM ammonium acetate (pH 5.5) containing 200 mM NaCl was applied to the products so obtained, to obtain recombinant altered HI-8 solutions which appeared as single bands on SDS-polyacrylamide-gels.

EXAMPLE 7

Purification of Expressed Peptide and Recovery on Activity Thereof 2-mercaptoethanol (Wako) was added, to become 1% of final concentration thereof, to each crude solution of the recombinant altered HI-8 prepared according to Example 6. The solutions were left for one hour at room temperature, applied to a column (16×1000 mm) filled with Sephacryl S-100HR (Pharmacia) equilibrated with 20 mM Tris-HCl buffer (pH 8.5) containing 200 mM NaCl, and gel-filtrated with the eluted buffer so obtained. Then, 2 ml of eluted fraction (containing 500 μg purified peptide), which appeared as a single band of approximately 8 kDa molecular weight on SDS-polyacrylamide gel electrophoresis, was added to 14 ml of solution for recovering the activity [solution containing 50 mM Tris-HCl (pH 8.5), 1M NaCl, 1 mM EDTA, 2 mM reduced glutathione, 0.2 mM oxidized glutathione]. Then 50 μg protein disulfide isomerase (Takara-Shuzo) was added, and reacted for 15 to 20 hours at room temperature. The activity was concentrated and the products so obtained desalted by using a membrane for ultrafiltration. The recombinant altered HI-8 peptides were purified by ion-exchange chromatography and gel-filtration, and these were used as samples having recovered activity.

EXAMPLE 8

Determination of Inhibitory Activity Against Human Neutrophil Elastase and Bovine Pancrease Trypsin Determination of Ki value of the samples of purified peptides of Example 7 against human neutrophil elastase was accomplished as follows.

10 μl of solution of human neutrophil elastase (Attends Research), (the concentration of which was adjusted to 25 μM with the following buffer), and 10 μl of test sample (the concentration of which was appropriately adjusted) were added to buffer containing 30 μl of 100 mM Tris-HCl (pH 7.5), 500 mM NaCl, 0.01% BSA, and left for 20 minutes at 30° C. Then, 200 μl of MeOSuc-Ala-Ala-Pro-Val-7AMC solution (Cambridge Research Biochemicals) containing 1% dimethyl-sulfoxide (hereinafter referred to as "DMSO") was added to the mixture to adjust the concentration thereof to 0.2 mM, 0.3 mM and 0.4 mM, and reacted at 30° C. Fluorescence at 450 nm excited at 365 nm was measured over 0 to 3 minutes with a spectrophotofluorometer (F-3000, HITACHI), and an initial reaction velocity was calculated. Ki value was determined by preparing a graph having a vertical axis of the reciprocal of initial reaction velocity and a horizontal axis of sample concentration, and then plotting on the graph lines for each of the three substrate concentrations and reading the intersection point of the three lines so obtained.

Furthermore, the Ki value against trypsin was determined as follows.

Firstly, buffer containing 20 μl of 10 mM $CaCl_2$, 50 mM Tris-HCl (pH 8.0) was mixed with 10 μl of test sample (1.2~6 μM) and 10 μl of 4.2 μM bovine pancreas trypsin solution (prepared by dissolving bovine pancreas trypsin in 1 mM HCl; Washington Biochemicals), and incubated at 30° C. for three minutes. 110 μl of 1M Tris-HCl (pH 8.0) buffer containing 100 mM $CaCl_2$ was added to this solution, then 350 μl of any of 0.6 mM, 1.2 mM and 2.3 mM Bz-DL-Arg-pNA.HCl (Nakaraitesk) solution (containing 10% DMSO) was added, and reacted at 30° C. Change on absorbance at 405 nm over time was recorded, and the initial reaction velocity of the enzyme was determined therefrom. Then, the Ki value against trypsin was determined according to a procedure which was similar to the procedure for human neutrophil elastase above.

The Ki value, obtained by the above procedures, of α 1-AT, UTI, recombinant HI-8 (R15), recombinant HI-8 (R15G3), and altered HI-8 peptides of the present invention against human neutrophil elastase are listed in the following Table 2.

Ki values of UTI, recombinant HI-8 (R15), recombinant HI-8 (R15G3) against bovine pancreas trypsin which are not referred to in the Table, were $9.2×10^{-7}M$, $3.6×10^{-7}M$ respectively. There was no inhibitory activity against bovine pancreas trypsin by the altered HI-8 peptides of the present invention.

TABLE 2

| Inhibitor (Altered Peptide) | Inhibitory Activity against Human Neutrophil Elastase Ki(M) |
| --- | --- |
| α 1-AT | $3.1 × 10^{-9}$ |
| UTI | $1.2 × 10^{-7}$ |
| R15 | $6.9 × 10^{-7}$ |
| R15G3 | $6.5 × 10^{-7}$ |
| I15G3 | $2.1 × 10^{-9}$ |

TABLE 2-continued

| Inhibitor (Altered Peptide) | Inhibitory Activity against Human Neutrophil Elastase Ki(M) |
|---|---|
| L15G3 | $4.1 \times 10^{-9}$ |
| V15G3 | $3.3 \times 10^{-9}$ |
| V15G3E11 | $1.2 \times 10^{-9}$ |
| V15G3Q46 | $2.5 \times 10^{-9}$ |
| V15G3E11Q46 | $8.0 \times 10^{-10}$ |
| I15G3E11 | $1.8 \times 10^{-9}$ |
| I15G3Q46 | $1.7 \times 10^{-9}$ |
| I15G3E11Q46 | $6.0 \times 10^{-10}$ |
| I15G3F18 | $2.5 \times 10^{-9}$ |

As shown by the results of Table 2 and those on trypsin inhibitory activity aforementioned, in comparison with non-altered recombinant HI-8, there was little inhibitory activity against bovine pancrease trypsin by a recombinant peptides wherein the fifteenth arginine in the recombinant HI-8 was replaced with isoleucine, leucine or valine; the inhibitory activity has therefore been remarkably reduced. Further, the Ki value against human neutrophil elastase of said altered peptides were reduced from $\frac{1}{168}$ to $\frac{1}{150}$ of the activity of recombinant HI-8 (R15); there were therefore remarkable increase in the inhibitory activity thereof. In particular, it was discovered that, in addition to an alteration of the fifteenth position, by further altering the eleventh position with glutamic acid and the forty-sixth position with glutamine, the Ki value against human neutrophil elastase can be reduced to $6 \sim 8 \times 10^{-10}$M.

EXAMPLE 9

Resistance Agains Oxidizer

5 μl of peptide sample, the concentration of which was adjusted appropriately, was mixed with 5 μl of 5 mM chloro-succinate-imide [prepared by dissolving chloro-succinate-imide (Nakaraitesk) in 100 mM Tris-HCl (pH 7.5) buffer containing 500 mM NaCl], then left for 10 minutes at room temperature, and then treated with the oxidizer. Then, 5 μl of human neutrophil elastase, concentration of which was adjusted with said buffer, and 35 μl of said buffer were further added thereto, and left for 15 minutes at 30° C. 450 μl of MeOSuc-Ala-Ala-Pro-Val-pNA (Cambridge Research Bio-Chemicals) solution (containing 1% DMSO), the concentration of which was adjusted to 0.1 mM with said buffer, was added thereto and further reacted for 30 minutes at 30° C. 40 μl of acetic acid was added and absorbance at 405 nm was measured. An inhibition against an activity of human neutrophil elastase in the samples treated with the oxidizer was indicated as an inhibitory rate (%) calculated by the following formula.

$$\text{Inhibitory Rate (\%)} = \frac{A - B}{A} \times 100$$

A: Absorbance obtained from sample not containing inhibitor.

B: Absorbance obtained from sample containing inhibitor.

Inhibitory rates (%) of α 1-AT, UTI and altered HI-8 peptides of the present invention against human neutrophil elastase, prepared respectively through the foregoing procedures and treated with the oxidizer are listed in the following Table 3.

TABLE 3

| Inhibitor (Altered Peptide) | Amount of Inhibitor (p mole) | Inhibitory Rate against Human Neutrophil Elastase (%) | |
|---|---|---|---|
| | | Concentration of chloro-succinate-imide (mM) | |
| | | 0 | 2.5 |
| α 1-AT | 10 | 100 | 6 |
| UTI | 20 | 72 | 5 |
| I15G3 | 5 | 84 | 74 |
| L15G3 | 5 | 84 | 74 |
| V15G3 | 5 | 93 | 87 |
| V15G3E11 | 5 | 97 | 92 |
| V15G3Q46 | 5 | 97 | 97 |
| V15G3E11Q46 | 5 | 95 | 94 |
| I15G3E11 | 5 | 87 | 87 |
| I15G3Q46 | 5 | 94 | 94 |
| I15G3E11Q46 | 5 | 92 | 94 |
| I15G3F18 | 5 | 92 | 90 |

The Table shows that the inhibitory activity of recombinant altered peptide of the present invention against human neutrophil elastase was retained under conditions wherein α 1-AT and UTI are oxidized and inactivated completely.

As stated above, the novel peptides of the invention which inhibit elastase are useful as a drug for prevention and treatment of diseases involving elastase, such as pulmonary emphysema, because the peptides exhibit a strong inhibitory activity against human neutrophil elastase and, in comparison with the native elastase inhibitor and chemically synthesized low molecular weight elastase inhibitor, a strong resistance against oxidization, lower immunogenicity, and less toxicity to humans.

We claim:
1. A peptide having an elastase inhibitory activity comprising an amino acid sequence of:

(SEQ ID NO: 1)

Thr—Val—Gly—Ala—Cys—Asn—Leu—Pro—Val—Ile—X11—
Gly—Pro—Cys—X15—Ala—Phe—X18—Gln—Leu—Trp—Ala—
Phe—Asp—Ala—Val—Lys—Gly—Lys—Cys—Val—Leu—Phe—
Pro—Tyr—Gly—Gly—Cys—Gln—Gly—Asn—Gly—Asn—Lys—
Phe—X46—Ser—Glu—Lys—Glu—Cys—Arg—Glu—Tyr—Cys—
Gly—Val—Pro—Gly—Asp—Glu—Asp—Glu—Leu—Leu, wherein
X11 is Arg or Glu;
X15 is Ile, Leu or Val;
X18 is Ile or Phe; and
X46 is Tyr or Gln.

2. The peptide according to claim 1, wherein said amino acid sequence is;

Thr—Val—Gly—Ala—Cys—Asn—Leu—Pro—Val—Ile—Arg—Gly—Pro—Cys—
Ile—Ala—Phe—Ile—Gln—Leu—Trp—Ala—Phe—Asp—Ala—Val—Lys—Gly—
Lys—Cys—Val—Leu—Phe—Pro—Tyr—Gly—Gly—Cys—Gln—Gly—Asn—Gly—
Asn—Lys—Phe—Tyr—Ser—Glu—Lys—Glu—Cys—Arg—Glu—Tyr—Cys—Gly—
Val—Pro—Gly—Asp—Glu—Asp—Glu—Glu—Leu—Leu.

3. The peptide according to claim 1, wherein said amino acid sequence is;

Thr—Val—Gly—Ala—Cys—Asn—Leu—Pro—Val—Ile—Arg—Gly—Pro—Cys—
Leu—Ala—Phe—Ile—Gln—Leu—Trp—Ala—Phe—Asp—Ala—Val—Lys—Gly—
Lys—Cys—Val—Leu—Phe—Pro—Tyr—Gly—Gly—Cys—Gln—Gly—Asn—Gly—
Asn—Lys—Phe—Tyr—Ser—Glu—Lys—Glu—Cys—Arg—Glu—Tyr—Cys—Gly—
Val—Pro—Gly—Asp—Glu—Asp—Glu—Glu—Leu—Leu.

4. The peptide according to claim 1, wherein said amino acid sequence is;

Thr—Val—Gly—Ala—Cys—Asn—Leu—Pro—Val—Ile—Arg—Gly—Pro—Cys—
Val—Ala—Phe—Ile—Gln—Leu—Trp—Ala—Phe—Asp—Ala—Val—Lys—Gly—
Lys—Cys—Val—Leu—Phe—Pro—Tyr—Gly—Gly—Cys—Gln—Gly—Asn—Gly—
Asn—Lys—Phe—Tyr—Ser—Glu—Lys—Glu—Cys—Arg—Glu—Tyr—Cys—Gly—
Val—Pro—Gly—Asp—Glu—Asp—Glu—Glu—Leu—Leu.

5. The peptide according to claim 1, wherein said amino acid sequence is;

Thr—Val—Gly—Ala—Cys—Asn—Leu—Pro—Val—Ile—Glu—Gly—Pro—Cys—
Val—Ala—Phe—Ile—Gln—Leu—Trp—Ala—Phe—Asp—Ala—Val—Lys—Gly—
Lys—Cys—Val—Leu—Phe—Pro—Tyr—Gly—Gly—Cys—Gln—Gly—Asn—Gly—
Asn—Lys—Phe—Tyr—Ser—Glu—Lys—Glu—Cys—Arg—Glu—Tyr—Cys—Gly—
Val—Pro—Gly—Asp—Glu—Asp—Glu—Glu—Leu—Leu.

6. The peptide according to claim 1, wherein said amino acid sequence is;

Thr—Val—Gly—Ala—Cys—Asn—Leu—Pro—Val—Ile—Arg—Gly—Pro—Cys—
Val—Ala—Phe—Ile—Gln—Leu—Trp—Ala—Phe—Asp—Ala—Val—Lys—Gly—
Lys—Cys—Val—Leu—Phe—Pro—Tyr—Gly—Gly—Cys—Gln—Gly—Asn—Gly—
Asn—Lys—Phe—Gln—Ser—Glu—Lys—Glu—Cys—Arg—Glu—Tyr—Cys—Gly—
Val—Pro—Gly—Asp—Glu—Asp—Glu—Glu—Leu—Leu.

7. The peptide according to claim 1, wherein said amino acid sequence is;

Thr—Val—Gly—Ala—Cys—Asn—Leu—Pro—Val—Ile—Glu—Gly—Pro—Cys—
Val—Ala—Phe—Ile—Gln—Leu—Trp—Ala—Phe—Asp—Ala—Val—Lys—Gly—
Lys—Cys—Val—Leu—Phe—Pro—Tyr—Gly—Gly—Cys—Gln—Gly—Asn—Gly—
Asn—Lys—Phe—Gln—Ser—Glu—Lys—Glu—Cys—Arg—Glu—Tyr—Cys—Gly—
Val—Pro—Gly—Asp—Glu—Asp—Glu—Glu—Leu—Leu.

8. The peptide according to claim 1, wherein said amino acid sequence is;

Thr—Val—Gly—Ala—Cys—Asn—Leu—Pro—Val—Ile—Glu—Gly—Pro—Cys—
Ile—Ala—Phe—Ile—Gln—Leu—Trp—Ala—Phe—Asp—Ala—Val—Lys—Gly—
Lys—Cys—Val—Leu—Phe—Pro—Tyr—Gly—Gly—Cys—Gln—Gly—Asn—Gly—
Asn—Lys—Phe—Tyr—Ser—Glu—Lys—Glu—Cys—Arg—Glu—Tyr—Cys—Gly—
Val—Pro—Gly—Asp—Glu—Asp—Glu—Glu—Leu—Leu.

9. The peptide according to claim 1, wherein said amino acid sequence is;

Thr—Val—Gly—Ala—Cys—Asn—Leu—Pro—Val—Ile—Arg—Gly—Pro—Cys—
Ile—Ala—Phe—Ile—Gln—Leu—Trp—Ala—Phe—Asp—Ala—Val—Lys—Gly—
Lys—Cys—Val—Leu—Phe—Pro—Tyr—Gly—Gly—Cys—Gln—Gly—Asn—Gly—
Asn—Lys—Phe—Gln—Ser—Glu—Lys—Glu—Cys—Arg—Glu—Tyr—Cys—Gly—
Val—Pro—Gly—Asp—Glu—Asp—Glu—Glu—Leu—Leu.

10. The peptide according to claim 1, wherein said amino acid sequence is;

Thr—Val—Gly—Ala—Cys—Asn—Leu—Pro—Val—Ile—Glu—Gly—Pro—Cys—
Ile—Ala—Phe—Ile—Gln—Leu—Trp—Ala—Phe—Asp—Ala—Val—Lys—Gly—
Lys—Cys—Val—Leu—Phe—Pro—Tyr—Gly—Gly—Cys—Gln—Gly—Asn—Gly—
Asn—Lys—Phe—Gln—Ser—Glu—Lys—Glu—Cys—Arg—Glu—Tyr—Cys—Gly—
Val—Pro—Gly—Asp—Glu—Asp—Glu—Glu—Leu—Leu.

11. The peptide according to claim 1, wherein said amino acid sequence is;

Thr—Val—Gly—Ala—Cys—Asn—Leu—Pro—Val—Ile—Arg—Gly—Pro—Cys—
Ile—Ala—Phe—Phe—Gln—Leu—Trp—Ala—Phe—Asp—Ala—Val—Lys—Gly—
Lys—Cys—Val—Leu—Phe—Pro—Tyr—Gly—Gly—Cys—Gln—Gly—Asn—Gly—
Asn—Lys—Phe—Tyr—Ser—Glu—Lys—Glu—Cys—Arg—Glu—Tyr—Cys—Gly—
Val—Pro—Gly—Asp—Glu—Asp—Glu—Glu—Leu—Leu.

12. A gene which codes for an amino acid sequence of:

Thr—Val—Gly—Ala—Cys—Asn—Leu—Pro—Val—Ile—X11—Gly—Pro—Cys—
X15—Ala—Phe—X18—Gln—Leu—Trp—Ala—Phe—Asp—Ala—Val—Lys—Gly—
Lys—Cys—Val—Leu—Phe—Pro—Tyr—Gly—Gly—Cys—Gln—Gly—Asn—Gly—
Asn—Lys—Phe—X46—Ser—Glu—Lys—Glu—Cys—Arg—Glu—Tyr—Cys—Gly—
Val—Pro—Gly—Asp—Glu—Asp—Glu—Glu—Leu—Leu,  (SEQ ID NO: 1)

wherein

X11 is Arg or Glu;

X15 is Ile, Leu or Val;

X18 is Ile or Phe; and

X46 is Tyr or Gln.

13. A plasmid comprising a gene which codes for an amino acid sequence of:

Thr—Val—Gly—Ala—Cys—Asn—Leu—Pro—Val—Ile—X11—Gly—Pro—Cys—
X15—Ala—Phe—X18—Gln—Leu—Trp—Ala—Phe—Asp—Ala—Val—Lys—Gly—
Lys—Cys—Val—Leu—Phe—Pro—Tyr—Gly—Gly—Cys—Gln—Gly—Asn—Gly—
Asn—Lys—Phe—X46—Ser—Glu—Lys—Glu—Cys—Arg—Glu—Tyr—Cys—Gly—
Val—Pro—Gly—Asp—Glu—Asp—Glu—Glu—Leu—Leu,  (SEQ ID NO: 1)

wherein

X11 is Arg or Glu;

X15 is Ile, Leu or Val;

X18 is Ile or Phe; and

X46 is Tyr or Gln.

14. A host microorganism having a plasmid comprising a gene which codes for an amino acid sequence of:

Thr—Val—Gly—Ala—Cys—Asn—Leu—Pro—Val—Ile—X11—Gly—Pro—Cys—
X15—Ala—Phe—X18—Gln—Leu—Trp—Ala—Phe—Asp—Ala—Val—Lys—Gly—
Lys—Cys—Val—Leu—Phe—Pro—Tyr—Gly—Gly—Cys—Gln—Gly—Asn—Gly—
Asn—Lys—Phe—X46—Ser—Glu—Lys—Glu—Cys—Arg—Glu—Tyr—Cys—Gly—
Val—Pro—Gly—Asp—Glu—Asp—Glu—Glu—Leu—Leu,  (SEQ ID NO: 1)

wherein

X11 is Arg or Glu;

X15 is Ile, Leu or Val;

X18 is Ile or Phe; and

X46 is Tyr or Gln.

15. The host microorganism according to claim 14, wherein said amino acid sequence is;

Thr—Val—Gly—Ala—Cys—Asn—Leu—Pro—Val—Ile—Arg—Gly—Pro—Cys—
Ile—Ala—Phe—Ile—Gln—Leu—Trp—Ala—Phe—Asp—Ala—Val—Lys—Gly—
Lys—Cys—Val—Leu—Phe—Pro—Tyr—Gly—Gly—Cys—Gln—Gly—Asn—Gly—
Asn—Lys—Phe—Tyr—Ser—Glu—Lys—Glu—Cys—Arg—Glu—Tyr—Cys—Gly—
Val—Pro—Gly—Asp—Glu—Asp—Glu—Glu—Leu—Leu.

16. The host microorganism according to claim 15, wherein said host microorganism is *Escherichia coli* JM109-pCD17I15G3 (FERM BP-4556).

17. The host microorganism according to claim 14, wherein said amino acid sequence is;

Thr—Val—Gly—Ala—Cys—Asn—Leu—Pro—Val—Ile—Arg—Gly—Pro—Cys—
Val—Ala—Phe—Ile—Gln—Leu—Trp—Ala—Phe—Asp—Ala—Val—Lys—Gly—
Lys—Cys—Val—Leu—Phe—Pro—Tyr—Gly—Gly—Cys—Gln—Gly—Asn—Gly—
Asn—Lys—Phe—Gln—Ser—Glu—Lys—Glu—Cys—Arg—Glu—Tyr—Cys—Gly—
Val—Pro—Gly—Asp—Glu—Asp—Glu—Glu—Leu—Leu.

18. The host microorganism according to claim 17, wherein said host microorganism is *Escherichia coli* JM109-pCD17V15G3Q46 (FERM BP-4557).

19. The host microorganism according to claim 14, wherein said amino acid sequence is;

Thr—Val—Gly—Ala—Cys—Asn—Leu—Pro—Val—Ile—Glu—Gly—Pro—Cys—
Val—Ala—Phe—Ile—Gln—Leu—Trp—Ala—Phe—Asp—Ala—Val—Lys—Gly—
Lys—Cys—Val—Leu—Phe—Pro—Tyr—Gly—Gly—Cys—Gln—Gly—Asn—Gly—
Asn—Lys—Phe—Gln—Ser—Glu—Lys—Glu—Cys—Arg—Glu—Tyr—Cys—Gly—
Val—Pro—Gly—Asp—Glu—Asp—Glu—Glu—Leu—Leu.

20. The host microorganism according to claim 19, wherein said host microorganism is *Escherichia coli* JM109-pCD17V1563E11Q46 (FERM BP- 560).

21. The host microorganism according to claim 14, wherein said amino acid sequence is;

Thr—Val—Gly—Ala—Cys—Asn—Leu—Pro—Val—Ile—Arg—Gly—Pro—Cys—
Ile—Ala—Phe—Ile—Gln—Leu—Trp—Ala—Phe—Asp—Ala—Val—Lys—Gly—
Lys—Cys—Val—Leu—Phe—Pro—Tyr—Gly—Gly—Cys—Gln—Gly—Asn—Gly—
Asn—Lys—Phe—Gln—Ser—Glu—Lys—Glu—Cys—Arg—Glu—Tyr—Cys—Gly—
Val—Pro—Gly—Asp—Glu—Asp—Glu—Glu—Leu—Leu.

22. The host microorganism according to claim 21, wherein said host microorganism is *Escherichia coli* JM109-pCD17I15G3Q46 (FERM BP-4558).

23. The host microorganism according to claim 14, wherein said amino acid sequence is;

Thr—Val—Gly—Ala—Cys—Asn—Leu—Pro—Val—Ile—Glu—Gly—Pro—Cys—
Ile—Ala—Phe—Ile—Gln—Leu—Trp—Ala—Phe—Asp—Ala—Val—Lys—Gly—
Lys—Cys—Val—Leu—Phe—Pro—Tyr—Gly—Gly—Cys—Gln—Gly—Asn—Gly—
Asn—Lys—Phe—Gln—Ser—Glu—Lys—Glu—Cys—Arg—Glu—Tyr—Cys—Gly—
Val—Pro—Gly—Asp—Glu—Asp—Glu—Glu—Leu—Leu.

24. The host microorganism according to claim 23, wherein said host microorganism is *Escherichia coli* JM109-pCD17I1563E11Q46 (FERM BP- 4559).

25. A peptide product having an elastase inhibitory activity produced by a host microorganism having a plasmid comprising a gene which codes for an amino acid sequence of:

Thr—Val—Gly—Ala—Cys—Asn—Leu—Pro—Val—Ile—X11—Gly—Pro—Cys—
X15—Ala—Phe—X18—Gln—Leu—Trp—Ala—Phe—Asp—Ala—Val—Lys—Gly—
Lys—Cys—Val—Leu—Phe—Pro—Tyr—Gly—Gly—Cys—Gln—Gly—Asn—Gly—
Asn—Lys—Phe—X46—Ser—Glu—Lys—Glu—Cys—Arg—Glu—Tyr—Cys—Gly—
Val—Pro—Gly—Asp—Glu—Asp—Glu—Glu—Leu—Leu, (SEQ ID NO: 1)

wherein

X11 is Arg or Glu;

X15 is Ile, Leu or Val;

X18 is Ile or Phe; and

X46 is Tyr or Gln.

26. A method for producing a peptide product having an elastase inhibitory activity produced by a host microorganism having a plasmid comprising a gene which codes for an amino acids sequence of:

Thr—Val—Gly—Ala—Cys—Asn—Leu—Pro—Val—Ile—X11—Gly—Pro—Cys—
X15—Ala—Phe—X18—Gln—Leu—Trp—Ala—Phe—Asp—Ala—Val—Lys—Gly—
Lys—Cys—Val—Leu—Phe—Pro—Tyr—Gly—Gly—Cys—Gln—Gly—Asn—Gly—
Asn—Lys—Phe—X46—Ser—Glu—Lys—Glu—Cys—Arg—Glu—Tyr—Cys—Gly—
Val—Pro—Gly—Asp—Glu—Asp—Glu—Glu—Leu—Leu, (SEQ ID NO: 1)

wherein

X11 is Arg or Glu;

X15 is Ile, Leu or Val;

X 18 is Ile or Phe; and

X46 is Tyr or Gln.

* * * * *

UNITED STATES PATENT AND TRADEMARK OFFICE
CERTIFICATE OF CORRECTION

PATENT NO. : 5,541,288
DATED : July 30, 1996
INVENTOR(S) : Nakano *et al.*

It is certified that error appears in the above-identified patent and that said Letters Patent is hereby corrected as shown below:

Column 2, line 64 delete "a";

Column 3, line 24 insert --the-- before amino;

Column 3, line 67 insert --and-- before valine;

Column 4, line 8 insert --the-- before amino;

Column 4, line 37 insert --an-- before animal;

Column 6, line 36 replace "370" with --37--;

Column 8, line 31 delete "it";

Column 12, line 54 replace "$9.2 \times 10^{-7}$" with --$9.2 \times 10^{-8}$--;

Column 13, line 18 delete "a";

Column 13, line 25 replace "increase" with --increases--

Other publications, add --Ohnishi et al. "Effects of Urinary Trypsin Inhibitor on Pancreatic Enzymes and Experimental Acute Pancreatitis", *Digest. Dis. Sci.*:26-32 (1984)--.

Signed and Sealed this

Fifteenth Day of February, 2000

Attest:

Q. TODD DICKINSON

*Attesting Officer*  *Commissioner of Patents and Trademarks*

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 66 amino acids
        ( B ) TYPE: amino acid
        ( D ) TOPOLOGY: unknown ( i i ) MOLECULE TYPE: Protein ( i x ) FEATURE:
        ( A ) NAME/KEY: mutation (B) LOCATION: 3
                (C) IDENTIFICATION METHOD: E
                (D) OTHER INFORMATION: Ala or Gly
                (A) NAME/KEY: mutation
                (B) LOCATION: 11
                (C) IDENTIFICATION METHOD: E
                (D) OTHER INFORMATION: Arg or Glu
                (A) NAME/KEY: mutation
                (B) LOCATION: 15
                (C) IDENTIFICATION METHOD: E
                (D) OTHER INFORMATION: Arg, Val, Ile or Leu
                (A) NAME/KEY: mutation
                (B) LOCATION: 18
                (C) IDENTIFICATION METHOD: E
                (D) OTHER INFORMATION: Ile or Phe
                (A) NAME/KEY: mutation
                (B) LOCATION: 46
                (C) IDENTIFICATION METHOD: E
                (D) OTHER INFORMATION: Tyr or Gln (xi) SEQUENCE DESCRIPTION: SEQ ID NO:1:

```
Thr  Val  Xaa  Ala  Cys  Asn  Leu  Pro  Val  Ile  Xaa  Gly  Pro  Cys  Xaa  Ala
 1                    5                         10                        15

Phe  Xaa  Gln  Leu  Trp  Ala  Phe  Asp  Ala  Val  Lys  Gly  Lys  Cys  Val  Leu
               20                        25                        30

Phe  Pro  Tyr  Gly  Gly  Cys  Gln  Gly  Asn  Gly  Asn  Lys  Phe  Xaa  Ser  Glu
               35                        40                        45

Lys  Glu  Cys  Arg  Glu  Tyr  Cys  Gly  Val  Pro  Gly  Asp  Glu  Asp  Glu  Glu
      50                        55                        60

Leu  Leu
 65
```

(2) INFORMATION FOR SEQ ID NO:2:

(i) SEQUENCE CHARACTERISTICS:
          (A) LENGTH: 259 base pairs
          (B) TYPE: nucleic acid
          (C) STRANDEDNESS: Double
          (D) TOPOLOGY: linear (ii) MOLECULE TYPE: Other nucleic acid, Synthesized DNA (ix) FEATURE:
          (A) NAME/KEY: CDS
          (B) LOCATION: 1..201
          (C) IDENTIFICATION METHOD: E
          (A) NAME/KEY: mat peptide
          (B) LOCATION: 1..198
          (C) IDENTIFICATION METHOD: E
          (A) NAME/KEY: terminator
          (B) LOCATION: 210..242
          (C) IDENTIFICATION METHOD: S
          (A) NAME/KEY: inhibitory-site
          (B) LOCATION: 43..45
          (C) IDENTIFICATION METHOD: S (xi) SEQUENCE DESCRIPTION: SEQ ID NO:2:

```
ACG  GTT  GCT  GCT  TGC  AAC  CTG  CCG  GTT  ATC  CGT  GGT  CCG  TGC  CGT  GCT    48
Thr  Val  Ala  Ala  Cys  Asn  Leu  Pro  Val  Ile  Arg  Gly  Pro  Cys  Arg  Ala
 1                    5                         10                        15

TTC  ATC  CAG  CTG  TGG  GCT  TTC  GAC  GCT  GTT  AAA  GGT  AAA  TGC  GTT  CTG    96
Phe  Ile  Gln  Leu  Trp  Ala  Phe  Asp  Ala  Val  Lys  Gly  Lys  Cys  Val  Leu
               20                        25                        30

TTC  CCG  TAT  GGT  GGT  TGC  CAG  GGT  AAC  GGT  AAC  AAA  TTC  TAT  TCT  GAA   144
Phe  Pro  Tyr  Gly  Gly  Cys  Gln  Gly  Asn  Gly  Asn  Lys  Phe  Tyr  Ser  Glu
               35                        40                        45

AAA  GAA  TGC  CGT  GAA  TAT  TGC  GGT  GTT  CCG  GGT  GAC  GAA  GAC  GAA  GAA   192
Lys  Glu  Cys  Arg  Glu  Tyr  Cys  Gly  Val  Pro  Gly  Asp  Glu  Asp  Glu  Glu
      50                        55                        60
```

```
CTG  CTG  TGATGATCTA  GAGCCCAGCC  CGCCTAATGA  GCGGGCTTTT  TTTTGAACAA         248
Leu  Leu
 65

AAGGCGGAATT                                                                   259
```

( 2 ) INFORMATION FOR SEQ ID NO:3:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: Other nucleic acid, Synthesized DNA ( x i ) SEQUENCE DESCRIPTION: SEQ ID NO:3:

```
GGTTGCTGCT  TGCAACCTGC  CGGTTATCCG  TGGTCCGTGC  CGTGCTTTCA  T                 51
```

( 2 ) INFORMATION FOR SEQ ID NO:4:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: Other nucleic acid, Synthesized DNA ( x i ) SEQUENCE DESCRIPTION: SEQ ID NO:4:

```
CCAGCTGTGG  GCTTTCGACG  CTGTTAAAGG  TAAATGCGTT  CTGTTCCCGT                    50
```

( 2 ) INFORMATION FOR SEQ ID NO:5:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: Other nucleic acid, Synthesized DNA ( x i ) SEQUENCE DESCRIPTION: SEQ ID NO:5:

```
ATGGTGGTTG  CCAGGGTAAC  GGTAACAAAT  TCTATTCTGA  AAAAGAATGC  CG                52
```

( 2 ) INFORMATION FOR SEQ ID NO:6:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: Other nucleic acid, Synthesized DNA ( x i ) SEQUENCE DESCRIPTION: SEQ ID NO:6:

```
TGAATATTGC  GGTGTTCCGG  GTGACGAAGA  CGAAGAACTG  CTGTGATGAT                    50
```

( 2 ) INFORMATION FOR SEQ ID NO:7:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: Other nucleic acid, Synthesized DNA ( x i ) SEQUENCE DESCRIPTION: SEQ ID NO:7:

```
CTAGAGCCCA  GCCCGCCTAA  TGAGCGGGCT  TTTTTTTGAA  CAAAAGGCGG                    50
```

( 2 ) INFORMATION FOR SEQ ID NO:8:

( i ) SEQUENCE CHARACTERISTICS:
    ( A ) LENGTH: 63 base pairs
    ( B ) TYPE: nucleic acid
    ( C ) STRANDEDNESS: single
    ( D ) TOPOLOGY: linear ( i i ) MOLECULE TYPE: Other nucleic acid, Synthesized DNA ( x i ) SEQUENCE DESCRIPTION: SEQ ID NO:8:

ACAGCTGGAT GAAAGCACGG CACGGACCAC GGATAACCGG CAGGTTGCAA GCAGCAACCG    60

TAC    63

( 2 ) INFORMATION FOR SEQ ID NO:9:

( i ) SEQUENCE CHARACTERISTICS:
    ( A ) LENGTH: 51 base pairs
    ( B ) TYPE: nucleic acid
    ( C ) STRANDEDNESS: single
    ( D ) TOPOLOGY: linear ( i i ) MOLECULE TYPE: Other nucleic acid, Synthesized DNA ( x i ) SEQUENCE DESCRIPTION: SEQ ID NO:9:

AACCACCATA CGGGAACAGA ACGCATTTAC CTTTAACAGC GTCGAAAGCC C    51

( 2 ) INFORMATION FOR SEQ ID NO:10:

( i ) SEQUENCE CHARACTERISTICS:
    ( A ) LENGTH: 51 base pairs
    ( B ) TYPE: nucleic acid
    ( C ) STRANDEDNESS: single
    ( D ) TOPOLOGY: linear ( i i ) MOLECULE TYPE: Other nucleic acid, Synthesized DNA ( x i ) SEQUENCE DESCRIPTION: SEQ ID NO:10:

AATATTCACG GCATTCTTTT TCAGAATAGA ATTTGTTACC GTTACCCTGG C    51

( 2 ) INFORMATION FOR SEQ ID NO:11:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( i i ) MOLECULE TYPE: Other nucleic acid, Synthesized DNA ( x i ) SEQUENCE DESCRIPTION: SEQ ID NO:11:

TGGGCTCTAG ATCATCACAG CAGTTCTTCG TCTTCGTCAC CCGGAACACC GC    52

( 2 ) INFORMATION FOR SEQ ID NO:12:

( i ) SEQUENCE CHARACTERISTICS:
    ( A ) LENGTH: 44 base pairs
    ( B ) TYPE: nucleic acid
    ( C ) STRANDEDNESS: single
    ( D ) TOPOLOGY: linear ( i i ) MOLECULE TYPE: Other nucleic acid, Synthesized DNA ( x i ) SEQUENCE DESCRIPTION: SEQ ID NO:12:

AATTCCGCCT TTTGTTCAAA AAAAAGCCCG CTCATTAGGC GGGC    44

( 2 ) INFORMATION FOR SEQ ID NO:13:

( i ) SEQUENCE CHARACTERISTICS:
  ( A ) LENGTH: 64 base pairs
  ( B ) TYPE: nucleic acid
  ( C ) STRANDEDNESS: single
  ( D ) TOPOLOGY: linear ( i i ) MOLECULE TYPE: Other nucleic acid, Synthesized DNA ( i x ) FEATURE:
  ( A ) NAME/KEY: sig peptide
  ( B ) LOCATION: 2..64
  ( C ) IDENTIFICATION METHOD: S
  ( D ) OTHER INFORMATION: Coding Strand of Synthesized DNA which codes Omp A Signal Peptide. BspHI Adhesive-End and Blunt-End is produced by annealing it with Sequence of SEQ. ID. NO.14.

( x i ) SEQUENCE DESCRIPTION: SEQ ID NO:13:

```
C ATG AAA AAA ACC GCT ATC GCT ATC GCT GTT GCT CTG GCT GGT TTT        46
  Met Lys Lys Thr Ala Ile Ala Ile Ala Val Ala Leu Ala Gly Phe
  1               5                   10                  15

GCT ACC GTT GCT CAG GCC                                               64
Ala Thr Val Ala Gln Ala
                20
```

( 2 ) INFORMATION FOR SEQ ID NO:14:

( i ) SEQUENCE CHARACTERISTICS:
    ( A ) LENGTH: 60 base pairs
    ( B ) TYPE: nucleic acid
    ( C ) STRANDEDNESS: single
    ( D ) TOPOLOGY: linear ( i i ) MOLECULE TYPE: Other nucleic acid, Synthesized DNA ( i x ) FEATURE:
    ( A ) NAME/KEY: sig peptide
    ( B ) LOCATION: 1..60
    ( C ) IDENTIFICATION METHOD: S
    ( D ) OTHER INFORMATION: Complementary Strand is formed with Sequence of SEQ. ID. NO.13.

( x i ) SEQUENCE DESCRIPTION: SEQ ID NO:14:

GGCCTGAGCA ACGGTAGCAA AACCAGCCAG AGCAACAGCG ATAGCGATAG CGGTTTTTTT        60

( 2 ) INFORMATION FOR SEQ ID NO:15:

( i ) SEQUENCE CHARACTERISTICS:
    ( A ) LENGTH: 18 amino acids
    ( B ) TYPE: amino acid
    ( D ) TOPOLOGY: linear ( i i ) MOLECULE TYPE: Peptide ( x i ) SEQUENCE DESCRIPTION: SEQ ID NO:15:

```
Ser Glu Lys Glu Cys Arg Glu Tyr Cys Gly Val Pro Gly Asp Glu Asp
1               5                   10                  15
Glu Glu
```

( 2 ) INFORMATION FOR SEQ ID NO:16:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: Other nucleic acid, Synthesized DNA ( i x ) FEATURE:
    ( A ) NAME/KEY: mutation (B) LOCATION: 7..9
(C) IDENTIFICATION METHOD: S
(D) OTHER INFORMATION: Third amino acid of Recombinant HI-8 is
 converted into Glycine.

(xi) SEQUENCE DESCRIPTION: SEQ ID NO:16:

ACGGTTGGTG CTTGCAAC  18

(2) INFORMATION FOR SEQ ID NO:17:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: Other nucleic acid, Synthesized DNA (ix) FEATURE:
      (A) NAME/KEY: mutation
      (B) LOCATION: 10..12
      (C) IDENTIFICATION METHOD: S
      (D) OTHER INFORMATION: 15th amino acid of Recombinant HI-8 is
        converted into Isoleucine.

(xi) SEQUENCE DESCRIPTION: SEQ ID NO:17:

GGTCCGTGCA TTGCTTTCAT C  21

(2) INFORMATION FOR SEQ ID NO:18:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: Other nucleic acid, Synthesized DNA (ix) FEATURE:
      (A) NAME/KEY: mutation
      (B) LOCATION: 10..12
      (C) IDENTIFICATION METHOD: S
      (D) OTHER INFORMATION: 15th amino acid of Recombinant HI-8 is
        converted into Leucine.

(xi) SEQUENCE DESCRIPTION: SEQ ID NO:18:

GGTCCGTGCC TGGCTTTCAT C  21

(2) INFORMATION FOR SEQ ID NO:19:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: Other nucleic acid, Synthesized DNA (ix) FEATURE:
      (A) NAME/KEY: mutation
      (B) LOCATION: 10..12
      (C) IDENTIFICATION METHOD: S
      (D) OTHER INFORMATION: 15th amino acid of Recombinant HI-8 is
        converted into Valine.

(xi) SEQUENCE DESCRIPTION: SEQ ID NO:19:

GGTCCGTGCG TTGCTTTCAT C  21

(2) INFORMATION FOR SEQ ID NO:20:

(i) SEQUENCE CHARACTERISTICS:
      (A) LENGTH: 21 base pairs (B) TYPE: nucleic acid
(C) STRANDEDNESS: single
(D) TOPOLOGY: linear (ii) MOLECULE TYPE: Other nucleic acid, Synthesized DNA (ix) FEATURE:
(A) NAME/KEY: mutation
(B) LOCATION: 10..12
(C) IDENTIFICATION METHOD: S
(D) OTHER INFORMATION: 11th amino acid of Recombinant HI-8 is converted into Glutamic Acid.

(xi) SEQUENCE DESCRIPTION: SEQ ID NO:20:

CCGGTTATCG AAGGTCCGTG C                                                        21

(2) INFORMATION FOR SEQ ID NO:21:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: Other nucleic acid, Synthesized DNA (ix) FEATURE:
(A) NAME/KEY: mutation
(B) LOCATION: 17..19
(C) IDENTIFICATION METHOD: S
(D) OTHER INFORMATION: 46th amino acid of Recombinant HI-8 is converted into Glutamine.

(xi) SEQUENCE DESCRIPTION: SEQ ID NO:21:

TAACGGTAAC AAATTCCAGT CTGAAAAAGA ATGCCG                                         36

(2) INFORMATION FOR SEQ ID NO:22:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: Other nucleic acid, Synthesized DNA (ix) FEATURE:
(A) NAME/KEY: mutation
(B) LOCATION: 13..15
(C) IDENTIFICATION METHOD: S
(D) OTHER INFORMATION: 18th Amino Acid of Recombinant HI-8, wherein 15th Amino Acid was already altered to Isoleucine, is further converted into Phenylalanine.

(xi) SEQUENCE DESCRIPTION: SEQ ID NO:22:

TGCATTGCTT TCTTCCAGCT GTGG                                                      24